US008642053B2

(12) United States Patent
Faergemann et al.

(10) Patent No.: US 8,642,053 B2
(45) Date of Patent: Feb. 4, 2014

(54) POTENTIATED TOPICAL COMPOSITION

(75) Inventors: Jan Faergemann, Göteborg (SE); Thomas Hedner, Gällstad (SE)

(73) Assignee: Ambria Dermatology AB, Helsingborg (SE)

( * ) Notice: Subject to any disclaimer, the term of this patent is extended or adjusted under 35 U.S.C. 154(b) by 824 days.

(21) Appl. No.: 10/491,992

(22) PCT Filed: Oct. 18, 2002

(86) PCT No.: PCT/SE02/01908
§ 371 (c)(1),
(2), (4) Date: Aug. 9, 2004

(87) PCT Pub. No.: WO03/035021
PCT Pub. Date: May 1, 2003

(65) Prior Publication Data
US 2004/0248993 A1    Dec. 9, 2004

(30) Foreign Application Priority Data

Oct. 21, 2001 (SE) .................................. 0103528

(51) Int. Cl.
*A61K 8/02* (2006.01)
(52) U.S. Cl.
USPC ......................................................... 424/401
(58) Field of Classification Search
USPC ......................................................... 424/401
See application file for complete search history.

(56) References Cited

U.S. PATENT DOCUMENTS

| | | | | | |
|---|---|---|---|---|---|
| 3,979,463 | A | * | 9/1976 | Endres | 568/737 |
| 3,996,934 | A | * | 12/1976 | Zaffaroni | 424/434 |
| 4,254,104 | A | * | 3/1981 | Suzuki | 514/785 |
| 4,701,320 | A | * | 10/1987 | Hasegawa et al. | 424/54 |
| 4,756,906 | A | * | 7/1988 | Sweeny | 424/63 |
| 5,079,003 | A | * | 1/1992 | Scaffidi | 424/401 |
| 5,158,978 | A | * | 10/1992 | Rubin | 514/567 |
| 5,196,187 | A | * | 3/1993 | Nicoll et al. | 424/70.12 |
| 5,215,580 | A | * | 6/1993 | Elfenthal et al. | 106/441 |
| 5,369,129 | A | * | 11/1994 | Swanbeck et al. | 514/738 |
| 5,405,366 | A | * | 4/1995 | Fox et al. | 607/50 |
| 5,641,768 | A | * | 6/1997 | Loria | 514/182 |
| 5,698,589 | A | * | 12/1997 | Allen | 514/509 |
| 5,728,732 | A | * | 3/1998 | Corey et al. | 514/544 |
| 5,976,565 | A | * | 11/1999 | Fotinos | 424/448 |
| 6,117,436 | A | * | 9/2000 | Flemming et al. | 424/401 |
| 6,123,927 | A | * | 9/2000 | Ogawa et al. | 424/59 |
| 6,193,996 | B1 | | 2/2001 | Effing et al. | |

FOREIGN PATENT DOCUMENTS

| | | |
|---|---|---|
| DE | 198 57 491 A1 | 6/2000 |
| DE | 198 574 92 A1 | 6/2000 |
| EP | 1 000 542 A1 | 5/2000 |
| EP | 1000542 A1 * | 5/2000 ............ A01N 31/02 |
| EP | 1 033 127 A1 | 9/2000 |
| EP | 1 063 007 A1 | 12/2000 |
| EP | 1 166 762 A1 | 1/2002 |
| WO | WO-93/03697 A1 | 3/1993 |
| WO | WO 93/20812 | 10/1993 |
| WO | WO-95/05137 A1 | 2/1995 |
| WO | WO-98/27960 A2 | 7/1998 |
| WO | WO-99/51212 A2 | 10/1999 |
| WO | WO/00/66077 * | 11/2000 |
| WO | WO 00/72883 * | 12/2000 |
| WO | WO/00/72883 * | 12/2000 |
| WO | WO-00/76315 A1 | 12/2000 |
| WO | WO 01/07003 A1 | 2/2001 |

OTHER PUBLICATIONS

Sloan, Kenneth B. (Prodrugs: topical and ocular drug delivery.; New York; Marcel Dekker, Inc., 1992).*
Silverman, Richard. The Organic Chemistry of Drug Design and Drug Action. San Diego: Academic Press, Inc., 1992.*
JA Franklyn (BMJ vol. 300 Mar. 17, 1990:693-4).*
Susan Smolinske, Handbook of Food, Drug, and Cosmetic Excipients. CRC Press LLC. Boca Raton, Florida. 1992.*
Evenbratt et al. (Acta Derm Venereol 2009; 89: 126-129).*
CAS Registry No. 111-29-5 (SciFinder® ; CAS Registry No. 111-29-5: 1,5-pentanediol. American Chemical Society (Accessed Nov. 2012)).*
CAS Registry No. 57-55-6 (SciFinder® ; CAS Registry No. 57-55-6: 1,2-propanediol. American Chemical Society (Accessed Nov. 2012)).*
OECD. "Percutaneous Absorption Testing: Is There a Way to Consencus?" Organisation for Economic Co-operation and Development. Twelfth Meeting of the National Co-ordinators of the Test Guidelines Programme, May 19-17, 2000 to be held at the Château de la Muette, Paris, beginning at 16:30 on the 17th. ENV/JM/TG(2000)5. Dist.:Apr. 12, 2000:pp. 1-42.*
Sigma-Aldrich (Product Directory: Biochemicals and Reagents: Antibiotics: Chemical Structure Class. http://www.sigmaaldrich.com/chemistry/chemistry-products.html?TablePage=14836602:p. 1-2. Accessed Jul. 30, 2013.*

* cited by examiner

Primary Examiner — Jeffrey S. Lundgren
Assistant Examiner — Chris Simmons
(74) Attorney, Agent, or Firm — Arent Fox LLP

(57) ABSTRACT

A topical composition for skin care or administration of a pharmacologically active agent in form of a lotion, cream or similar comprises from 5% to 70% by weight of pentane-1, 5-diol and a cosmetically or pharmaceutically acceptable carrier, with the proviso that the composition does not comprise polysiloxane, volatile siloxane, phosphatidyl-choline, creatine, carnitine, panthenol, pyruvic acid, monoglyceride of lauric acid, monoglyceride of myristic acid. Also disclosed are corresponding methods of administration, a patch for holding said composition against the skin, and methods of preventing or treating a dry skin condition and of keeping skin in a humid state.

18 Claims, 1 Drawing Sheet

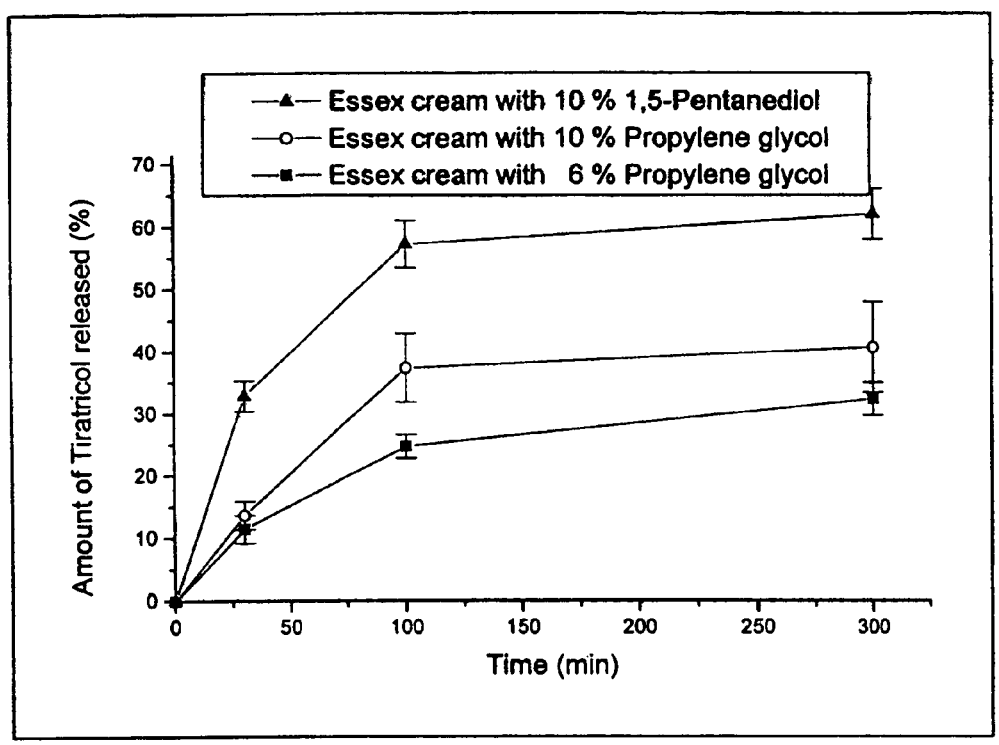
Release of tiratricol from Essex cream compositions

POTENTIATED TOPICAL COMPOSITION

FIELD OF THE INVENTION

The present invention relates to potentiated topical compositions, that is, topical compositions for cosmetic use or comprising a pharmacologically active agent, the cosmetic or pharmacological effect of which is potentiated by a carrier constituent which has little pharmacological effect per se.

BACKGROUND OF THE INVENTION

The penetration of the skin by pharmacologically active agents contained in compositions for topical administration usually is slow and often too slow to be of practical value. The methods known in the art to enhance penetration frequently use adjuvants or mixtures of adjuvants to enhance absorption. However many of the more effective adjuvants irritate the skin or are toxic or smelly or stain the clothes they come into contact with.

Pentane-1,5-diol is known to possess antiviral, antifungal and antibacterial activity, in particular antiviral activity against herpes simples virus (U.S. Pat. No. 5,369,129). Pentane-1,5-diol has been used as an adjuvant component in the transdermal administration of the antihypertensive drug prazosine (WO 93/03697) in combination with a sulfhydryl-containing compound and a fatty ester. U.S. Pat. No. 5,550,145 discloses an antimicrobial composition comprising a monoglyceride and 5% by weight of pentane-1,5-diol. U.S. Pat. No. 4,241,084 discloses an antibacterial and antifungal composition comprising a sulfonamide and an alkylene glycol containing from 5 to 8 carbon atoms and an alkylene glycol ester. WO 96/11572 discloses a antimicrobial composition comprising carboxylic acids of up to ten carbon atoms or their salts and $C_3$-$C_{10}$-diols. WO 93/20812 discloses an antimicrobial composition comprising a) monoglyceride of lauric acid, a monoglyceride of mono-myristic acid or their mixtures, an antibacterial substance and a diol with 3-6 carbon atoms. EP 0 884 045 A1 discloses a self-tanning skin composition comprising a self-tanning skin coloring agent, a polyethoxyalcohol, a polyol and, optionally, a pentanediol. WO 98/27960 discloses a viscous hydrogel composition for topical administration comprising a microbially active nitroimidazole drug, pentylene glycol and a hydroxyalkyl cellulose gelling agent and water, buffered to a physiologically acceptable pH. U.S. Pat. No. 5,879,690 discloses a composition for treatment of sagging subcutaneous muscle comprising an agent exhibiting or producing catecholamine activity and a carrier comprising skin penetration enhancer such as pentanediol. GB 2 280 111 A discloses clear gel antiperspirant compositions comprising an antiperspirant, pentanediol, a co-solvent of polyethylene glycol, water and/or glycerin, a buffering agent and a gelling agent.

Propylene glycol is a hygroscopic liquid widely used as a carrier in topical preparations. It is very hygroscopic and considered generally non-toxic (exception: ototoxicity) in contrast to ethylene glycol and hexylene-1,6-glycol (for a review, see: Goldsmith, L A. *Propylene glycol*. Int J Dermat 1978; 17:703-705).

OBJECTS OF THE INVENTION

It is an object of the invention to provide a composition for skin care which has improved properties in comparison to compositions known in the art, in particular compositions containing propane-1,2-diol as a carrier.

It is another object of the invention to provide a composition for topical administration of a pharmaceutically active agent which has improved properties in comparison to compositions known in the art, in particular compositions of this kind containing propane-1,2-diol.

It is an additional object of the invention to provide a composition for skin care and for topical administration of a pharmaceutical, the composition having improved moisture retaining properties.

Further objects of the invention are evident from the following summary of the invention, a number of preferred embodiments thereof, and the appended claims.

SUMMARY OF THE INVENTION

The present invention is based on the insight that propylene glycol can be advantageously substituted in many cosmetic and pharmaceutical compositions by pentane-1,5-diol.

According to the present invention is provided a topical composition for skin care or administration of a pharmacologically active agent comprising from 5% by weight to 70% by weight of pentane-1,5-diol and a cosmetically or pharmaceutically acceptable carrier, with the proviso that the composition does not contain any one of polysiloxane, volatile siloxane, phosphatidylcholine, creatine, carnitine, panthenol, pyruvic acid, mono-glyceride of lauric acid, and monoglyceride of myristic acid. It is preferred for the composition to comprise from 15% by weight to 40% by weight of pentane-1,5-diol, more preferred from 20-35% of pentane-1,5-diol. Preferably the cosmetically or pharmaceutically acceptable carrier comprises less than 20% or 10% by weight of propane-1,2-diol, glycerol or a combination thereof, more preferred less than 5% by weight of propane-1,2-diol, glycerol or a combination thereof, most preferred less than 1% by weight of propane-1,2-diol, glycerol or a combination thereof. The cosmetic or pharmaceutical composition preferably comprises from 0.1 to 30% by weight of water.

According to a first preferred aspect of the invention the cosmetic or pharmaceutical composition of the invention comprises a tonicity adjusting agent; from 0.1% by weight to 20% by weight of a moisturizing agent selected from carbamide, NaCl, lactic acid, and their combinations; from 0.1 to 30% by weight of polyethylene glycol; a UV-absorbing agent; a colorant selected from titanium dioxide, calcium carbonate, and zinc oxide; a fragrant agent.

According to a second preferred aspect of the invention, cosmetic or pharmaceutical composition is in the form of a cream, a liquid, a lotion, an ointment, a paste, a gel, a shampoo, a spray, a lipstick.

According to a third preferred aspect of the invention, the cosmetic or pharmaceutical composition is carried by a patch impregnated with it.

According to a fourth preferred aspect of the invention, the cosmetic of pharmaceutical composition comprises an anionic emulsifying wax, such as Cetylanum.

According to a fifth preferred aspect of the invention, the pharmaceutical composition comprises a pharmacologically active agent selected from steroids, antimycotic agents, agents for treating diseases of the thyroidea, antibiotics, antiviral agents, antihistamins, antiseptics, agents for the treatment of acne, agents for the treatment of warts, NSAIDs, COX2 selective agents, local anesthetics, agents for the treatment of psoriasis and eczema, cytostatics, polypeptides, TNF-α blockers, as well as other agents used in the treatment of diseases affecting the skin. Salicylic acid is a preferred pharmacologically agent.

According to a sixth preferred aspect of the invention, the cosmetic or pharmaceutical composition is provided in a sealed container.

According to a seventh preferred aspect of the invention is disclosed a cosmetic or medical patch provided with the composition of the invention; the patch is optionally enclosed in a sealed plastic envelope.

Furthermore is disclosed a method of topically administering a pharmaceutical agent, comprising forming a solution, emulsion, suspension, ointment or cream of a pharmacologically effective amount of said agent in a carrier comprising from 5% to 70% by weight of pentane-1,5-diol, followed by applying said solution, emulsion, suspension, ointment or cream to a selected site of the skin of a person to be treated for a condition or disease against which said pharmaceutical agent is effective. Preferably the administration comprises providing said composition on a patch or other suitable device for holding it against the selected skin site.

Also disclosed is a method of treating or preventing a dry skin condition, including dermatitis, the method comprising (i) providing a pharmaceutical composition in form of a solution, emulsion, suspension, ointment or cream, which comprises from 5% to 70% by weight of pentane-1,5-diol, and (ii) applying the solution, emulsion, suspension, ointment or cream to a selected site of the skin of a person to be treated. According to a preferred aspect of the invention the method comprises providing the composition on a patch (including absorbed by a patch) or other suitable device capable of being applied to the selected site of the skin, preferably for a period of time exceeding 6 hours and even 24 hours. It is preferred for the pharmaceutical composition used in the method not to contain any one of polysiloxane, volatile siloxane, phosphatidylcholine, creatine, carnitine, panthenol, pyruvic acid, mono-glyceride of lauric acid, and monoglyceride of myristic acid.

Furthermore is disclosed a method of preserving the skin of a person in a humid state, the method comprising (i) providing a cosmetic composition in form of a solution, emulsion, suspension, ointment or cream, which comprises from 5% to 70% by weight of pentane-1,5-diol, and (ii) applying the solution, emulsion, suspension, ointment or cream to the skin to be preserved in a humid state. It is preferred for the cosmetic composition used in the method not to comprise polysiloxane, volatile siloxane, phosphatidyl-choline, creatine, carnitine, panthenol, pyruvic acid, monoglyceride of lauric acid, monoglyceride of myristic acid.

Also disclosed is the use of pentane-1,5-diol for the manufacture of a medicament for preventing and/or treating a dry skin condition and for the manufacture of a cosmetic capable of preserving skin in a humid condition.

The composition of the present invention may also be used for storage and transport of organs and tissue, in particular skin tissue. Other uses are the treatment of various skin diseases, in particular where keratolytic properties are desired, optionally in combination with other keratolytic agents, such as salicylic acid and lactic acid. Further uses are as contact creams for EKG, ECG, TNS, and ultrasound measurements. The composition of the invention is also useful for skin protection against dehydration and in the treatment and prevention of dry skin, including the prevention of dermatitis.

DETAILED DESCRIPTION OF PREFERRED EMBODIMENTS

Example 1

Release of Tiratricol

In this study the thyroid hormone compound tiratricol was used due to its pharmacological effect on a number of skin conditions such as ichthyosis, psoriasis, acne, corticosteroid atrophy, and skin scarring (WO 96/40048).

Cream A: 0.1% by weight of powderous tiratricol was blended with 99.9% by weight of Essex cream containing 10% by weight of pentane-1,5-diol.

Cream B (cream according to the invention): 0.1% by weight of powderous tiratricol was blended with a mixture of 10% by weight of propane-1,2-diol and 89.9% by weight of Essex® cream base (Schering Plough).

Creams A and B were compared in respect of release of tiritricol in a multilayer membrane system for determining percutaneous absorption (Bronaught, R L and Stewart, R L, *Methods for in vitro percutaneous absorption studies III. Hydrophobic compounds*. J Pharm Soc 1984; 73:1255-1258); Bronaught R L et al., *Determination of Percutaneous Absorption by In Vitro Techniques*). Bronaught R L et al., *Methods for in vitro percutaneous absorption studies II. Comparison of human and animal skin*. Toxicol Appl Pharmacol 1982; 62:481-488; Bronaught R L et al., *Methods for in vitro percutaneous absorption studies VI. Preparation of the barrier layer*. J Pharm Sci 1986, 76:487-491). A Skin Penetration System 3-6 item # LG-1084-CS (3.0 ml cells) manufactured by Laboratory Glass Apparatus, Inc. (Berkeley, Calif., USA) was used. The results shown in Tables 1a-1c and FIG. 1 demonstrate the superior release of tiratricol from Cream A 62% by weight of which is released within 300 min in contrast to 41% by weight of tiratricol from Cream B.

TABLE 1a

Release of tiratricol (0.1% by weight) from a composition consisting, in addition, of 10% by weight of pentane-1,5-diol and 89.9% by weight of Essex-crème, in a multilayer membrane system

| Cream | Time (min) | Membrane 1 | Membrane 2 | Membrane 3 | Σ Membr. 1-3 | µg tiratricol released from 10 mg cream |
|---|---|---|---|---|---|---|
| | | Amount of tiratricol released (in %) | | | | |
| A | 30 | 14.65 (±1.85) | 10.87 (±1.09) | 7.35 (±0.36) | 32.88 (±2.47) | 2.98 (±0.22) |
| A | 100 | 25.30 (±2.94) | 17.53 (±1.55) | 14.39 (±3.79) | 57.22 (±3.79) | 5.19 (±0.34) |
| A | 300 | 26.14 (±0.77) | 19.06 (±3.19) | 16.87 (±1.78) | 62.06 (±4.02) | 5.63 (±0.36) |

TABLE 1b

Release of tiratricol (0.1% by weight) from a composition consisting, in addition, of 10% by weight of propane-1,2-diol and 89.9% by weight of Essex-crème, in a multilayer membrane system

| Cream | Time (min) | Membrane 1 | Membrane 2 | Membrane 3 | Σ Membr. 1-3 | µg tiratricol released from 10 mg cream |
|---|---|---|---|---|---|---|
| | | Amount of tiratricol released (in %) | | | | |
| B | 30 | 8.36 (±3.04) | 3.18 (±1.84) | 0.59 (±0.63) | 13.66 (±2.24) | 1.14 (±0.37) |
| B | 100 | 19.27 (±3.08) | 13.16 (±5.16) | 4.95 (±4.95) | 37.38 (±5.53) | 3.50 (±0.52) |
| B | 300 | 18.39 (±3.16) | 12.04 (±2.00) | 10.27 (±0.82) | 40.70 (±3.02) | 3.81 (±0.28) |

TABLE 1c

Release of tiratricol from Essex-cream comprising 6% and 10% of propane-1,2-diol and 10% (all by weight) of pentane-1,5-diol

| Time (min) | Propane-1,2-diol, 6% by weight | Propane-1,2-diol, 10% by weight (B) | pentane-1,5-diol, 10% by weight (A) |
|---|---|---|---|
| | Amount of tiratricol released (in %) | | |
| 30 | 11.43 (±2.23) | 13.66 (±2.24) | 32.88 (±2.47) |
| 100 | 24.70 (±1.89) | 37.38 (±5.53) | 57.22 (±3.79) |
| 300 | 36.94 (±2.72) | 40.70 (±3.02) | 62.06 (±4.02) |

Example 2

In Vitro Water Binding Capacity of Pentane-1,5-Diol, Propane-1,2-Diol, and Urea The water binding capacity of pentane-1,5-diol, propane-1,2-diol, and urea was investigated in vitro using pieces of human stratum corneum from a volunteer (for the method, see: Swanbeck, G. *A new treatment of ichthyosis and other hyperkeratotic conditions*. Acta derm.-venerol. 48:123-127, 1968). They were cut into pieces of about 3×3×0.5 mm and used as such. The specimens were immersed for 12 hours in distilled water, aqueous pentane-1,5-diol (10% by weight), aqueous propane-1,2-diol (10% by weight) or aqueous urea (10% by weight). The specimens then were blotted on filter paper and placed in a moisture over a saturated sodium tartrate solution providing a relative humidity of about 85% at 22° C. After 6 hrs the specimens were removed and weighed. Their water content at 6 h was obtained by subtracting the weight of the specimens dried for 24 hrs in a dry atmosphere at room temperature. The results are shown in Table 2. The water binding capacity after 6 hrs was 9% by weight for pentane-1,5-diol, 7% by weight for propane-1,2-diol, and 17% by weight for urea. An aqueous solution containing 20% of pentane-1,5-diol increased the water binding capacity to 13% by weight (water content 24%).

TABLE 2

Effect of water uptake of stratum corneum pieces pre-incubated with 10% (by weight) solutions of pentane-1,5-diol, propane-1,2-diol, and urea after 6 hrs of incubation in an atmosphere with a relative humidity of 85% at room temperature.

| Substance | Uptake of water after 6 hrs % (mg) | Dry weight (mg) |
|---|---|---|
| pentane-1,5-diol | 20% (0.0075) | 0.0062 |
| propane-1,2-diol | 18% (0.0032) | 0.0027 |
| urea | 28% (0.0109) | 0.0085 |
| distilled water (control) | 11% (0.0049) | 0.0044 |

Example 3

Acute Toxicity of Pentane-1,5-Diol (a) Acute toxicity was tested in Carworth-Wistar male rats weighing from 90 to 120 gr. The orally administered dose was logarithmically increased by a factor of 2. The diol was given as such and diluted in water, oil or agar. Mortality was investigated over a fortnight period; $LD_{50}$=5.89 g/kg body weight.

(b) Penetration of rabbit skin by pentane-1,5-diol was tested with a cuff model. The hair on the back of four male rabbits weighing from 2.5 to 3.5 kg was removed by shaving, the diol applied to the skin, and the skin occluded with plastic film for 24 hrs. The animals were immobilized during the test period. After the exposure the animals were observed over a fortnight period for mortality which was found to be higher than 20 ml/kg, the highest dose tested.

(c) Inhalation of pentane-1,5-diol. Six rats were made to breathe air saturated with the diol for a period of 8 hrs. None of the animals died.

Example 4

Skin and Eye Irritation Tests (a) The shaved skin of 5 albino rabbits was exposed to pentane-1,5-diol for 24 hours and the effect assessed using scale graded 1 (no irritation) to 10 (maximum irritation). Consistently a score of 1 was obtained.

(b) Pentane-1,5-diol was administered to the eye (conjunctiva) of five albino rabbits. Only very mild irritation (score 2 on a 1-10 scale) was observed.

Example 5

Medical Patch Provided with Composition A

A medical cotton patch (5×5×ca. 1 cm) backed by perforated polyethylene on one side was provided with about 3 g of composition A on its front side and positioned against the skin of a volunteer (upper left arm) for a period of 24 hrs. Upon removal the skin seemed free from irritation.

Example 6

Water Binding Capacity of Pentane-1,5-Diol

Dry skin is a problem in patients with atopic dermatitis, psoriasis, ichtyosis and many other dermatological disorders. Urea or a combination of urea and sodium chloride in various formulations (creams, lotions, etc.) have been used for many years to treat dry skin. One important problem with these formulations is itching and burning when they are applied on eczematous skin.

The aim of the present experiments was to evaluate the water binding capacity of pentane-1,5-diol in vitro, and to compare it with that of urea.

Pieces of stratum corneum from the sole of 7 healthy volunteers were used. They were cut into pieces of about 3×3×0.5 mm and used as such. The specimens were immersed for 12 hours in distilled water, aqueous pentane-1,5-diol (20% by weight), and aqueous urea (10% by weight). Thereafter the specimens were blotted on filter paper and placed in a moist chamber with a saturated sodium tartrate salt solution giving a relative humidity, in the chamber, of about 85%. The specimens were removed after 24 hours for weighing. The water content (WC) of the specimens at 24 hours was obtained by subtracting the weight of the specimen after drying for 24 hours in a dry atmosphere at room temperature.

The results are listed in Table 3. The water binding capacity was estimated by subtracting the WC for stratum corneum incubated with distilled water for 24 hours from the WC for the stratum corneum pieces incubated with the test substances for 24 hours. The water binding capacity after 24 hours was 23% (mean) for pentane-1,5-diol and 16% (mean) for urea. Thus, with the water binding composition of the invention containing 20% by weight of pentane-1,5-diol, a better water retaining effect was obtained than with an aqueous composition containing 10% by weight of urea. While the latter composition does give rise to itching when applied to eczematous skin, this negative effect is not encountered with the composition according to the invention.

TABLE 3

Effect on uptake of water in pieces of stratum corneum pre-incubated with a 20% solution (in distilled water) of pentan-1,5-diol and a 10% solution (in distilled water) of urea and distilled water, as a control, after 24 hours of incubation in an atmosphere with a relative humidity of 85%.

| Substance | Uptake of water in percent of dry weight after 24 hours incubation in 85% relative humidity | Water binding capacity |
|---|---|---|
| Pentane-1,5-diol | 43%, range 36-50% | 23% |
| Urea | 36%, range 24-47% | 16% |
| Distilled water (control) | 20%, range 14-24% | |

The invention claimed is:

1. A topical composition for administration of a pharmacologically active agent comprising a pharmacologically effective amount of said pharmacologically active agent, from 5% by weight to 35% by weight of pentane-1,5-diol and a cosmetically or pharmaceutically acceptable carrier, wherein the pharmacologically active agent is selected from the group consisting of steroids and thyroid hormones.

2. The composition of claim 1, in which the amount of pentane-1,5-diol is up to 20% by weight.

3. The composition of claim 1, in which the amount of pentane-1,5-diol is up to 15% by weight.

4. The composition of claim 1, wherein the cosmetically or pharmaceutically acceptable carrier comprises less than 20% by weight of propane-1,2-diol, glycerol or a combination thereof.

5. The composition of claim 4, comprising less than 5% by weight of propane-1,2-diol, glycerol or a combination thereof.

6. The composition of 5, wherein the cosmetically or pharmaceutically acceptable carrier comprises less than 1% by weight of propane-1,2-diol, glycerol or a combination thereof.

7. The composition of claim 1, comprising from 0.1 to 30% by weight of water.

8. The composition of claim 1, comprising from 0.1% by weight to 20% by weight of at least one material selected from the group consisting of carbamide, NaCl, and lactic acid.

9. The composition of claim 1, comprising from 0.1 to 30% by weight of polyethylene glycol.

10. The composition of claim 1, comprising a UV-absorbing agent.

11. The composition of claim 1, comprising an anionic emulsifying wax.

12. The composition of claim 1, in the form of a cream, a liquid, a lotion, an ointment, a paste, a gel, a shampoo, a spray, or a lipstick.

13. A patch impregnated with the composition of claims 1.

14. A topical composition for administration of a pharmacologically active agent comprising a pharmacologically effective amount of said pharmacologically active agent, from 5% by weight to 15% by weight of pentane-1,5-diol and a cosmetically or pharmaceutically acceptable carrier, wherein the composition is a cream in which the pharmacological active agent is a thyroid hormone.

15. The composition of claim 1, in which the pharmacological active is a steroid.

16. A patch impregnated with the composition of claim 14.

17. A patch impregnated with the composition of claim 15.

18. The composition of claim 1, wherein the composition does not comprise any one of polysiloxane, volatile siloxane, phosphatidylcholine, creatine, carnitine, panthenol, pyruvic acid, monoglyceride of lauric acid, and monoglyceride of myristic acid.

* * * * *